US008080037B2

(12) United States Patent
Butler et al.

(10) Patent No.: US 8,080,037 B2

(45) Date of Patent: Dec. 20, 2011

(54) SPINAL CROSS-CONNECTOR WITH SPINAL EXTENSOR MUSCLE CURVATURE

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 444 days.

(21) Appl. No.: 12/348,279

(22) Filed: Jan. 3, 2009

(65) Prior Publication Data

US 2009/0177234 A1 Jul. 9, 2009

Related U.S. Application Data

(60) Provisional application No. 61/010,008, filed on Jan. 4, 2008.

(51) Int. Cl.
*A61B 17/70* (2006.01)

(52) U.S. Cl. ........ 606/250; 606/251; 606/252; 606/253; 606/278

(58) Field of Classification Search .................. 606/246, 606/250–253, 260, 277, 278, 279
See application file for complete search history.

(56) References Cited

U.S. PATENT DOCUMENTS

| | | | | |
|---|---|---|---|---|
| 5,667,526 | A | 9/1997 | Levin | |
| 5,727,899 | A | 3/1998 | Dobrovolny | |
| 5,947,966 | A | 9/1999 | Drewry et al. | |
| 6,017,306 | A | 1/2000 | Bigliani et al. | |
| 6,096,039 | A | 8/2000 | Stoltenberg et al. | |
| 6,110,173 | A | 8/2000 | Thomas, Jr. | |
| 6,123,482 | A | 9/2000 | Keller | |
| 6,238,396 | B1 * | 5/2001 | Lombardo | 606/86 A |
| 6,311,586 | B1 | 11/2001 | Hirse | |
| 6,524,310 | B1 | 2/2003 | Lombardo et al. | |
| 6,616,664 | B2 | 9/2003 | Walulik et al. | |
| 6,736,775 | B2 | 5/2004 | Phillips | |
| 7,314,331 | B1 | 1/2008 | Koros et al. | |
| 7,553,279 | B1 | 6/2009 | Phillips et al. | |
| 7,666,210 | B2 | 2/2010 | Franck et al. | |
| 7,744,632 | B2 * | 6/2010 | Usher | 606/250 |
| 7,749,163 | B2 | 7/2010 | Mulac et al. | |
| 2003/0114853 | A1 | 6/2003 | Burgess et al. | |
| 2005/0113831 | A1 | 5/2005 | Franck et al. | |

(Continued)

OTHER PUBLICATIONS

Written Opinion of the International Search Authority for PCT Application No. PCT/US2008/069899, mailing date Sep. 8, 2008, 4 pages.

*Primary Examiner* — Eduardo C Robert
*Assistant Examiner* — Christina Negrelli
(74) *Attorney, Agent, or Firm* — Foley & Lardner LLP

(57) ABSTRACT

A spinal cross connector is configured for connection between spinal rods and provides allowance or space for spinal extensor muscles once the spinal process has been removed. The cross connector has curved first and second connection members that are adjustable in length and rotation relative to one another. A first clamping member is provided on the first connection member and defines first and second arcuate jaws that are adapted to clamp onto a first spinal rod. A second clamping member is provided on the second connection member and defines first and second arcuate jaws that are adapted to clamp onto a second spinal rod. Both the first and second clamping members are rotatable and thus provide the rotational adjustment. The cross-connector also provides easy in situ sizing and adjustability.

24 Claims, 4 Drawing Sheets

10 20 22 34 36 18 30 95 60 47 24 40 25 32 62 58 56 80 44 52 53 54 42 90 SP V 70

U.S. PATENT DOCUMENTS

2005/0228377 A1* 10/2005 Chao et al. ...................... 606/61
2006/0064093 A1 3/2006 Thramann et al.
2006/0206114 A1 9/2006 Ensign et al.
2006/0271045 A1 11/2006 Hubbard et al.
2007/0049932 A1 3/2007 Richelsoph et al.
2007/0233090 A1 10/2007 Naifeh et al.
2008/0086134 A1 4/2008 Butler et al.
2009/0228046 A1* 9/2009 Garamszegi .................. 606/278

* cited by examiner

SPINAL CROSS-CONNECTOR WITH SPINAL EXTENSOR MUSCLE CURVATURE

RELATED APPLICATIONS

This patent application claims the benefit of and/or priority to U.S. Provisional Patent Application Ser. No. 61/010,008 filed Jan. 4, 2008, entitled "Spinal Cross-Connector With Spinal Extensor Muscle Curvature" the entire contents of which is specifically incorporated herein by this reference.

BACKGROUND OF THE INVENTION

1. Field of the Invention

The present invention relates to spinal fixation devices and, in particular, to cross-connectors for connecting spinal fixation devices, such as spinal rods that are attached onto a patient's spine.

2. Background Information

There are many medical situations, because of disease, injury or deformity, where it is necessary to align and/or fix a desired relationship between adjacent vertebral bodies. In order to accomplish this goal, orthopedic spinal surgeons utilize spinal fixation devices to provide the desired relationship between adjacent vertebral bodies. Such spinal fixation devices typically include a spinal fixation element, such as a relatively rigid fixation rod, that is connected to adjacent vertebrae by attaching the rod to anchor devices implanted into the vertebrae.

Often, the spinal fixation rods are placed on opposite sides of the spinous process in a substantially parallel relationship. These spinal fixation rods may have pre-determined contours according to properties of the target implantation site. Once installed, the spinal fixation rods hold the vertebrae in a desired spatial relationship.

It may also be necessary in some circumstances to provide a spinal cross-connector at one or more points between the two spinal fixation rods in order to provide additional stability to the structure. Particularly, adjacent spinal fixation rod assemblies can be made more robust by using a cross-connector to bridge the pair of spinal rods.

While current spinal cross-connectors are effective, problems exist such as in mounting and maintaining the cross-connectors in a desired position and orientation with respect to the spinal rods. Other problems also exist with current cross-connectors such as sizing and locking issues. Moreover, current spinal cross-connectors do not allow room for extensor muscles of the spine. Particularly, the current spinal cross-connectors tend to constrict the spinal extensor muscles.

Accordingly, there presently exists a need for a spinal cross-connector that, when installed, provides allowance for spinal extensor muscles.

Moreover, there presently exists a need for a spinal cross-connector that, when installed, does not constrict spinal extensor muscles and/or allow the intrusion of the extensor muscles into the spinal cord space.

SUMMARY OF THE INVENTION

The present invention is a spinal cross-connector for connection between adjacent spinal rods that is configured to provide allowance for spinal extensor muscles. The present spinal cross-connector is curved relative to first and second spinal rod clamping members such that the curvature provides posterior clearance of the spinal extensor muscles.

The present cross-connector has first and second connection members or arms that are adjustably fixable in length relative to one another and in angularity relative to one another. The first connection member has a first spinal rod clamping member, clamp or clamshell rod attachment mechanism that is adapted to be connected, attached or affixed to one spinal rod while the second connection member, clamp or clamshell rod attachment has a second spinal rod clamping member that is adapted to be connected, attached or affixed to the other, adjacent spinal rod. The first and second connection members are curved relative to the respective first and second spinal rod clamping members, and thus the spinal rods, to where the connection members meet at a pivot, junction or juncture thereof. Rather than lying in the plane of the two spinal rods as do other spinal rod cross connectors, the curvature of the two connection members of the present spinal rod cross connector lies above (in a posterior direction) of the plane of the two spinal rods to provide clearance of the spinal extensor muscles.

Each spinal rod clamping member is rotatable relative to the respective connection member and thus the respective spinal rod. This allows the cross connector to be situated askew on the spinal rods thereby providing angling of the connection members. In addition to being length adjustable and in angle (as between the two spinal rods) the connection members may also rotate relative to the respective rod clamping member, once fixed on the spinal rod member, in order to provide angulation in two different directions about the rod clamping member.

Length adjustment is achieved through medial adjustment of the first and second connection members relative to each other by the first and second connection members having channels therein that receive a connection and fixation member. The connection and fixation member also provides a pivot for rotational adjustment of the first and second connection members relative to one another.

The cross-connector provides easily adjustable sizing (length and rotation) between adjacent spinal rods while maintaining spinal extensor muscle clearance or allowance.

The cross-connector also provides easy in situ sizing and adjustability.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A detailed description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

Figure 1:
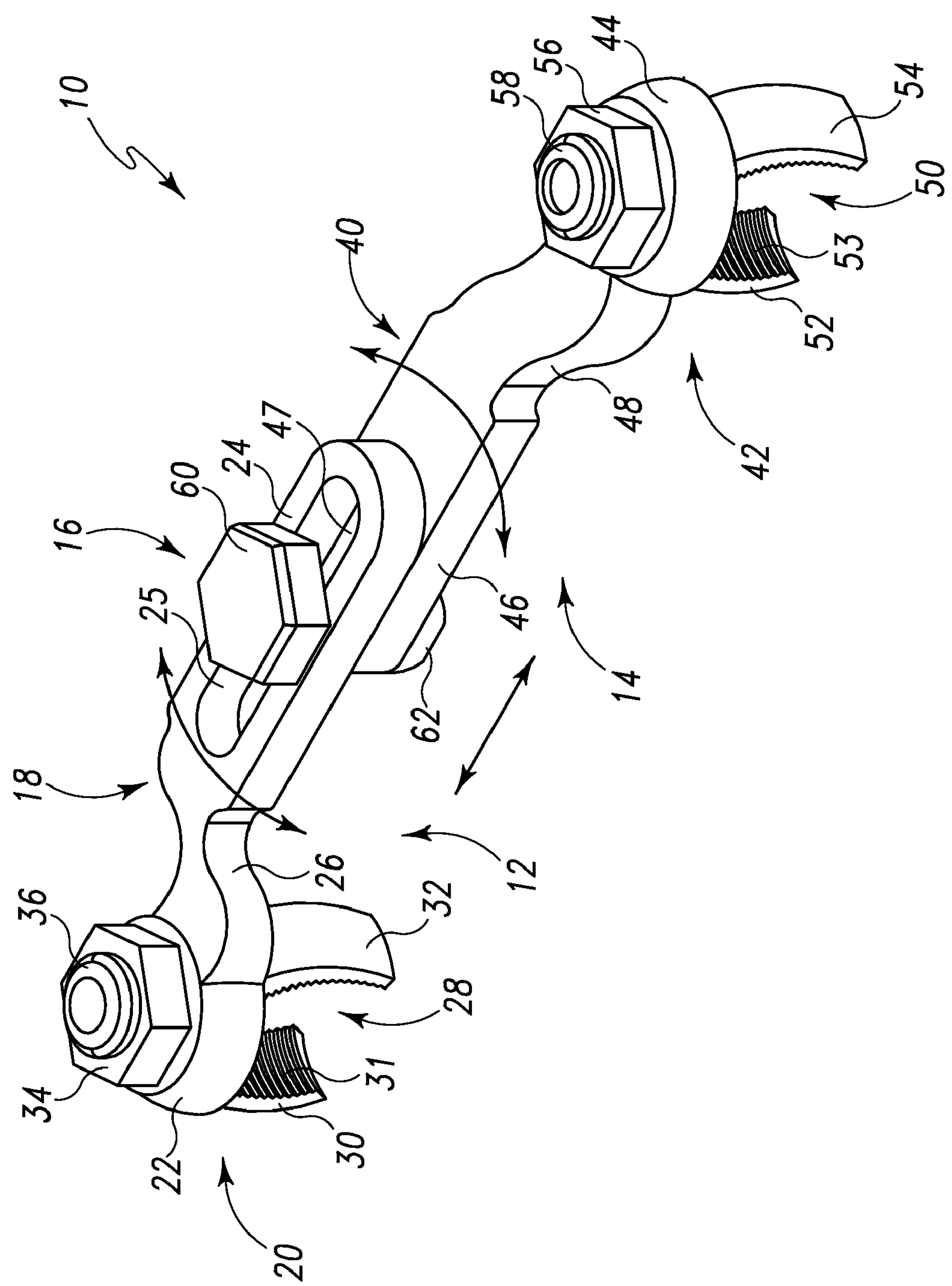
FIG. 1 is a perspective view of an exemplary spinal rod cross connector fashioned in accordance with the present principles.
Figure 2:
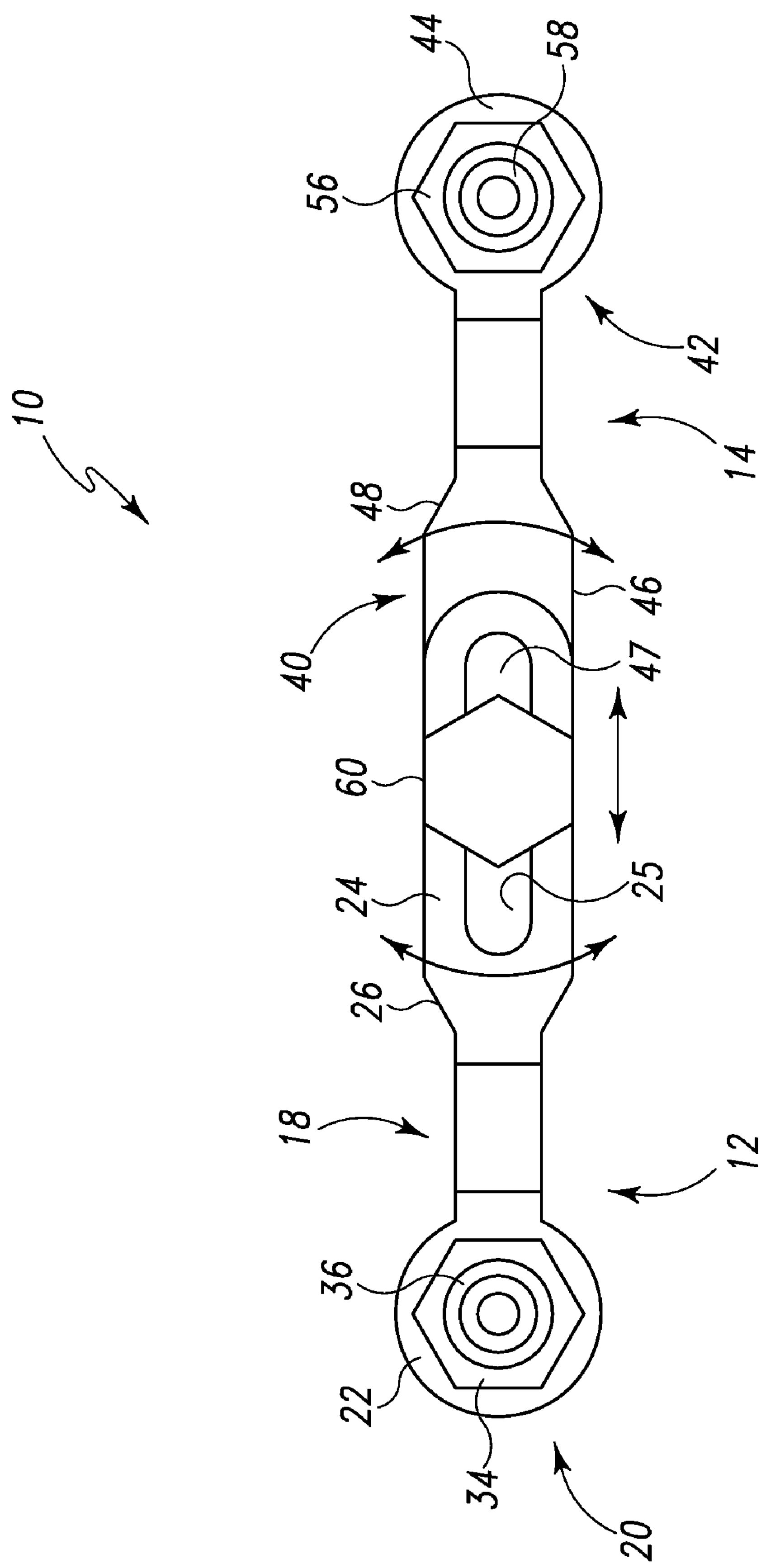
FIG. 2 is a top plan view of the spinal rod cross connector of FIG. 1.
Figure 3:
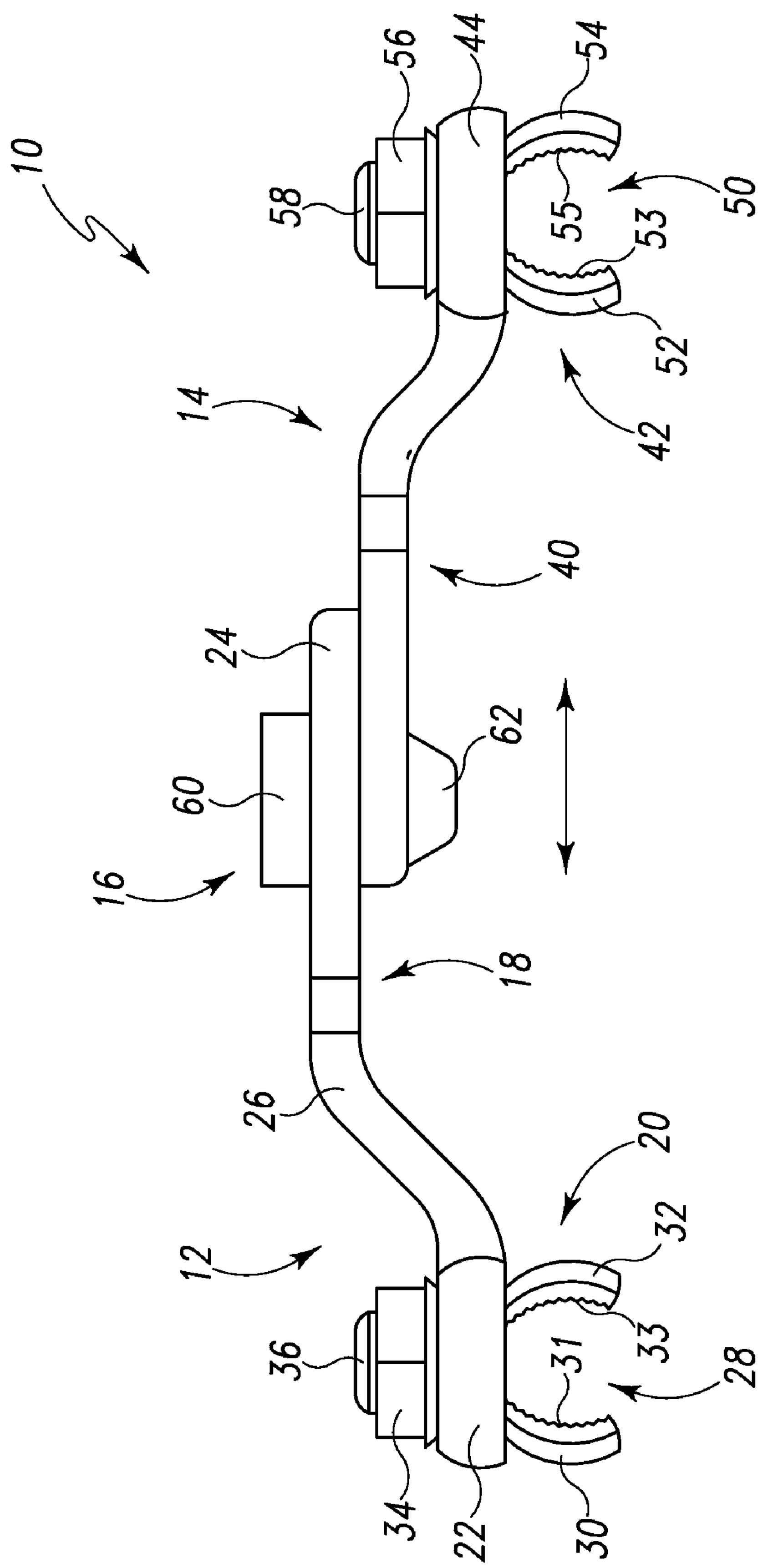
FIG. 3 is a side view of the spinal rod cross connector of FIG. 1.

Referring to FIGS. 1-3 there is depicted an exemplary embodiment of a spinal cross-connector generally designated 10 fashioned in accordance with the principles of the present invention. The spinal cross-connector 10 is made from a biocompatible material such as titanium, stainless steel or PEEK. However, other biocompatible materials or compounds may be used such as a polymer, plastic, metal alloy, composite or the like. The spinal cross-connector 10 is configured to provide allowance for and/or not constrict spinal extensor muscles when installed.

The spinal cross-connector 10 has a first connection member 12 and a second connection member 14 that are each adapted, configured and/or operable to connect to or clamp onto to respective spinal rods (not shown) and adjustably to each other as shown. The spinal cross-connector 10 is longitudinally adjustable as represented by the horizontal, double-headed arrow such that the span between the spinal rods is adjustable. The connection members 12 and 14 are also rotatably adjustable with respect to one another about a pivot/connection point defined by a pivot/retention/connection assembly 16 that is received in the channels 25 and 47 of the respective connection members 12, 14 and represented by the two, arced, double-headed arrows. The connection members 12, 14 are thus adjustably fixable in length relative to one another and in angularity relative to one another.

The first connection member 12 has an arm 18 with a clamping member 20 on one end thereof. The clamping member 20 has first and second arced jaws or members 30 and 32. The first jaw 30 includes teeth 31 on its inner arced surface. The second jaw 32 also includes teeth 33 on its inner arced surface. The first and second jaws 30, 32 are thus adapted, configured and/or operable to extend about a spinal rod with the teeth 31, 33 of the respective jaws 30, 32 holding onto the spinal rod.

An upper portion of the first and second jaws 30, 32 extend through a generally annular collar 22 of the first connection member 12 and terminate in a threaded shaft 36. The jaws 30 and 32 are rotatable about the collar 22. This allows the clamping member 20 to swivel about the spinal rod. The threaded shaft 36 of the clamping member 20 extends through the collar 22 and has a threaded nut 36 thereon for fixing the rotational alignment of the first and second jaws 30, 32. As the nut 36 is threadedly received and tightened onto the threaded shaft 36, the rotational orientation of the jaws 30, 32 is fixed relative to the collar 22. The nut 36 also fixates the clamping member 20 onto the rod. Prior to tightening of the nut 36, the clamping member 20 can be easily placed onto or removed from the rod and/or re-positioned along the axis of the rod.

The second connection member 14 has an arm 40 with a clamping member 42 on one end thereof. The clamping member 42 has first and second arced jaws or members 52 and 54. The first jaw 50 includes teeth 51 on its inner arced surface. The second jaw 54 also includes teeth 55 on its inner arced surface. The first and second jaws 52, 54 are thus adapted, configured and/or operable to extend about a spinal rod with the teeth 53, 55 of the respective jaws 52, 54 holding onto the spinal rod.

An upper portion of the first and second jaws 52, 54 extend through a generally annular collar 44 of the second connection member 14 and terminate in a threaded shaft 58. The jaws 52 and 54 are rotatable about the collar 44. This allows the clamping member 42 to swivel about the spinal rod. The threaded shaft 56 of the clamping member 42 extends through the collar 44 and has a threaded nut 58 thereon for fixing the rotational alignment of the first and second jaws 52, 54. As the nut 58 is threadedly received and tightened onto the threaded shaft 56, the rotational orientation of the jaws 52, 54 is fixed relative to the collar 44. The nut 58 also fixates the clamping member 42 onto the rod. Prior to tightening of the nut 58, the clamping member 42 can be easily placed onto or removed from the rod and/or re-positioned along the axis of the rod.

Each spinal rod clamping member 20, 42 is rotatable relative to the respective connection member 18, 40 and thus the respective spinal rod. This allows the cross connector to be situated askew on the spinal rods thereby providing angling of the connection members. In addition to being length adjustable and in angle (as between the two spinal rods) the connection members 18, 40 may also rotate relative to the respective rod clamping member 20, 42 to provide angulation in two different directions about the rod clamping member.

The arm 18 of the first connection member 12 includes a curved portion or section 26 that extends from the collar 22. The curved portion 26 defines its curvature posteriorly when the spinal cross-connector 10 is installed. The arm 18 also includes a connection portion or section 24 that extends from the curved portion 26. The connection portion 24 includes the longitudinal channel 25.

The arm 40 of the second connection member 14 includes a curved portion or section 48 that extends from the collar 44. The curved portion 48 defines its curvature posteriorly when the spinal cross-connector 10 is installed. The arm 40 also includes a connection portion or section 46 that extends from the curved portion 48. The connection portion 46 includes the longitudinal channel 47.

The curvature of the arms 18 and 40 provide clearance relative to the posterior of the spine or vertebra such that the spinal extensor muscles of the spine/vertebra are not constricted when the spinal cross-connector 10 is installed.

The longitudinal channel 25 of the arm 18 of the first connection member 12 aligns with the longitudinal channel 47 of the arm 40 of the second connection member 14. The pivot/retention assembly 16 is disposed in the longitudinal channels 25, 47 to provide the longitudinal or length adjustment as well as the rotational adjustment of the first and second connection members 12,14 and of the present cross connector 10. The pivot/retention assembly 16 includes a hex-head threaded screw 60 that receives a nut 62. The hex-head threaded screw 60 extends through the channels 25 and 47 to hold the arms 18 and 40 together when the nut 62 is tightened thereon. Particularly, the hex-head threaded screw fixes the position of the first and second connection members 12, 14 relative to one another.

The present spinal cross-connector 10 thus provides simple length adjustment and easy rotational clamping to adjacent spinal rods. This allows the present spinal cross-connector 10 to adjust to variations in spacing and skewness of adjacent spinal rods.

Figure 4:
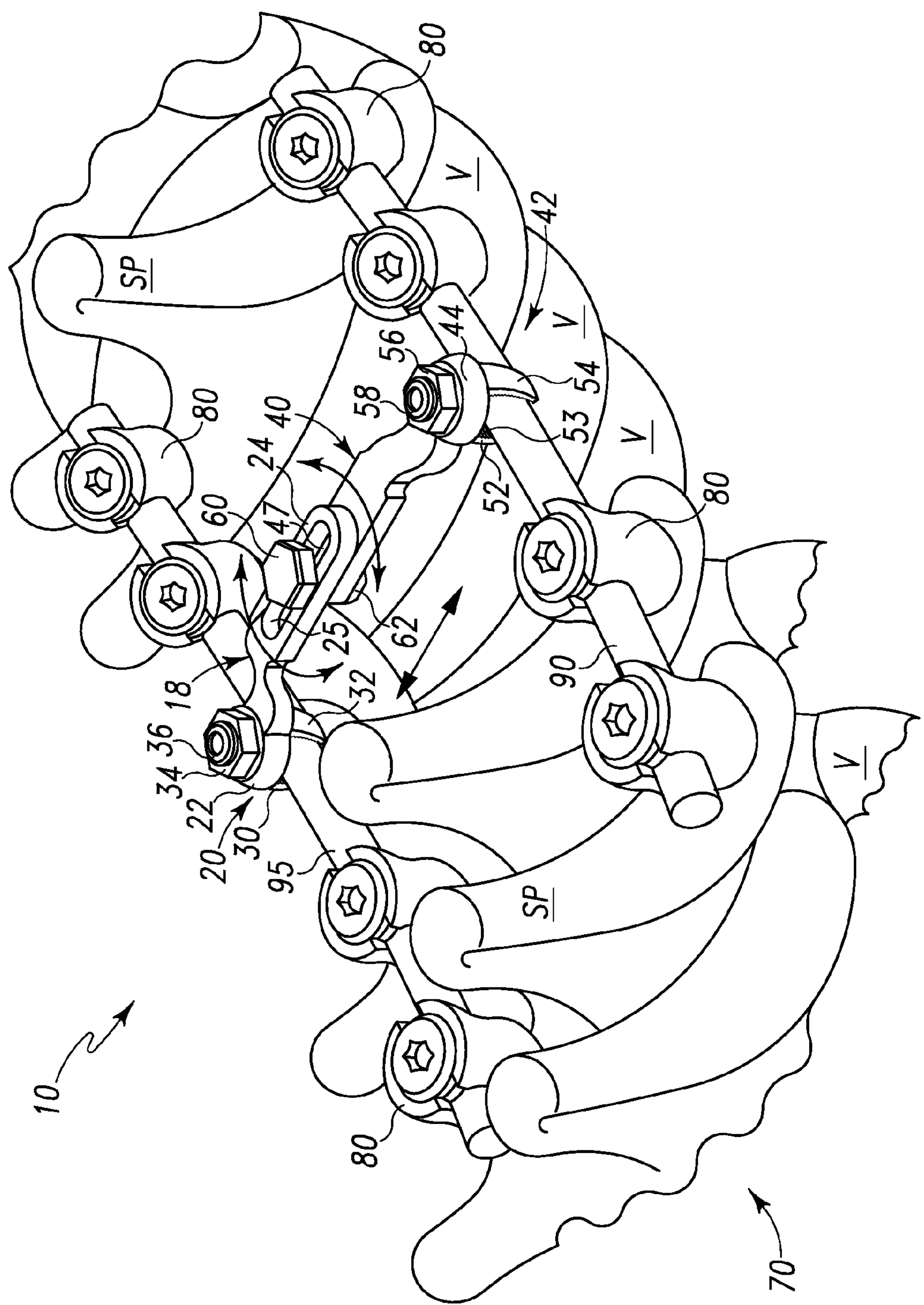
FIG. 4 is a perspective view of a portion of a human spine having undergone a spinal stabilization procedure involving removal of several spinous processes and the installation of spinal rod assemblies with a cross-connector of the present invention connected between the spinal rod assemblies.

FIG. 4 shows/depicts a posterior perspective view of a portion of a human spine 70 that has undergone a spinal stabilization procedure involving removal of several spinous processes (SP of vertebrae V) and the installation of two spinal rod assemblies thereon. The two spinal rod assemblies are positioned along the pedicles of the desired vertebrae, but may be mounted elsewhere. The spinal rod assemblies are provided for stabilization and spacing of the vertebrae V. Each spinal rod assembly consists of several screw constructs 80 and a spinal rod 95. The screw constructs 80 are affixed to the vertebra V, while the spinal rods 95 are oriented generally along the longitudinal axis of the spine. The present cross connector 10 is connected between the two spinal rod assemblies and, particularly to the spinal rods 95 thereof.

It can be seen that the connection members (arms) 12, 14 of the cross connector 10, rather than being straight, curve out in the posterior direction when attached to the spine rods 95. This curvature provides or allows space for the extensor muscle of the spine and, in some respects, mimics the spinous process that was removed. The angle, bend or curvature (i.e. 26 of 18, and 48 of 40) may be varied as desired to provide an overall arch or curvature. The coupling manner between the arms 12, 14 provide for variable angles therebetween. Additionally, it should be noted that while the connection assembly 16 is shown disposed at ends of the arms 12, 14, it can be positioned otherwise. Likewise, the particular retention member, the dimension(s) of the adjustment portion of the arm(s) and other features may be varied as desired. It should also be noted that more than one cross connector 10 may be used if desired.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal cross connector for connection between adjacent first and second spinal rods of a spinal rod assembly, the spinal cross connector comprising:

a first arm comprising a first clamping member portion, a first connection portion, and a first curved portion connecting the first clamping member portion and the first connection portion in an offset manner;

a second arm comprising a second clamping member portion, a second connection portion, and a second curved portion connecting the second clamping member portion and the second connection portion in an offset manner, the first and second arms pivotally coupled to one another via the first and second connection portions;

a first clamp disposed on the first clamping member portion of the first arm and adapted to affix to the first spinal rod; and a second clamp disposed on the second clamping member portion of the second arm and adapted to affix to the second spinal rod;

wherein the first and second connection portions are posteriorly offset relative to the first and second clamping member portions to provide posterior clearance of spinal extensor muscles when installed on a spine.

2. The spinal cross connector of claim 1, wherein the first and second arms are also length adjustable relative to one another.

3. The spinal cross connector of claim 2, wherein the first arm has a first longitudinal channel extending therethrough, the second arm has a second longitudinal channel extending therethrough, and further comprising a connector received in the first and second longitudinal channels.

4. The spinal cross connector of claim 3, wherein the connector is adapted to fix the length of the first and second arms relative to one another.

5. The spinal cross connector of claim 4, wherein the connector pivotally couples the first and second arms to one another.

6. The spinal cross connector of claim 5, wherein the connector fixes a pivot angle between the first and second arms.

7. The spinal cross connector of claim 2, wherein the first clamp is rotatable relative to the first arm and the second clamp is rotatable relative to the second arm.

8. The spinal cross connector of claim 7, wherein the first arm is rotatable relative to the first clamp when the first clamp is fixed to the first spinal rod and the second arm is rotatable relative to the second clamp when the second clamp is fixed to the second spinal rod.

9. The spinal cross connector of claim 1, wherein the first and second arms are formed of PEEK.

10. A spinal cross connector for connection between adjacent first and second spinal rods of a spinal rod assembly, the spinal cross connector comprising:

a first arm;

a second arm pivotally connected to the first arm at a pivot interface defined by interfacing surfaces of the first and second arms;

a first clamp disposed on an end of the first arm and adapted to affix to the first spinal rod;

a second clamp disposed on an end of the second arm and adapted to affix to the second spinal rod;

the first and second clamps disposed in a first plane adjacent the first and second spinal rods, and the interfacing surfaces of the pivot interface defining a second plane offset in a posterior direction from the first plane to provide for posterior clearance of spinal extensor muscles when installed on a spine.

11. The spinal cross connector of claim 10, wherein the first and second arms are also length adjustable relative to one another.

12. The spinal cross connector of claim 11, wherein the first arm has a first longitudinal channel extending therethrough, the second arm has a second longitudinal channel extending therethrough, and further comprising a connector received in the first and second longitudinal channels.

13. The spinal cross connector of claim 12, wherein the connector is adapted to fix the length of the first and second arms relative to one another.

14. The spinal cross connector of claim 13, wherein the connector pivotally couples the first and second arms to one another.

15. The spinal cross connector of claim 14, wherein the connector fixes a pivot angle between the first and second arms.

16. The spinal cross connector of claim 11, wherein the first clamp is rotatable relative to the first arm and the second clamp is rotatable relative to the second arm.

17. The spinal cross connector of claim 16, wherein the first arm is rotatable relative to the first clamp when the first clamp is fixed to the first spinal rod and the second arm is rotatable relative to the second clamp when the second clamp is fixed to the second spinal rod.

18. The spinal cross connector of claim 10, wherein the first and second arms are formed of PEEK.

19. A spinal cross connector comprising:

a first arm having a first length defined by a first clamping portion connected to a first connecting portion via a curved portion;

a second arm having a second length defined by a second clamping portion connected to a second connecting portion via a second curved portion, the first and second arms pivotally connected to one another;

a first clamp rotatably disposed on an end of the first arm and adapted to affix to the first spinal rod;

a second clamp rotatably disposed on an end of the second arm and adapted to affix to the second spinal rod;

wherein the first and curved portions offset the first and second connecting in a posterior direction relative to the first and second connecting portions to provide posterior clearance of spinal extensor muscles.

20. The spinal cross connector of claim 19, wherein the first and second arms are also length adjustable relative to one another.

21. The spinal cross connector of claim 20, wherein the first arm has a first longitudinal channel extending therethrough along a portion of its first lengths. the second arm has a second longitudinal channel extending therethrough along a portion of its second length, and further comprising a connector received in the first and second longitudinal channels.

22. The spinal cross connector of claim 21, wherein the connector is adapted to fix the length and pivot angle of the first and second arms relative to one another.

23. The spinal cross connector of claim 22, wherein the first clamp is rotatable relative to the first arm and the second clamp is rotatable relative to the second arm.

24. The spinal cross connector of claim 23, wherein the first arm is rotatable relative to the first clamp when the first clamp is fixed to the first spinal rod and the second arm is rotatable relative to the second clamp when the second clamp is fixed to the second spinal rod.

* * * * *